United States Patent
Paranhos

(10) Patent No.: US 9,603,961 B2
(45) Date of Patent: Mar. 28, 2017

(54) EQUIPMENT FOR SANITIZING THE AIR CONDITIONING SYSTEM OF VEHICLES BY MEANS OF RADIANT CATALYTIC IONIZATION

(71) Applicants: ECOQUEST DO BRASIL, Sao Paulo (BR); DBG GROUP INVESTMENTS, LLC, Dallas, TX (US)

(72) Inventor: Frederico M. Paranhos, Sao Paulo (BR)

(73) Assignees: DBG Group Investments, LLC, Dallas, TX (US); ECOQUEST DO BRASIL, COMERCIO IMPORTACAO EXPORTACAO E SERVICCOS PARA PURIFICACAO DE AR E AGUA LTDA, Sao Paulo (BR)

( * ) Notice: Subject to any disclaimer, the term of this patent is extended or adjusted under 35 U.S.C. 154(b) by 0 days.

(21) Appl. No.: 14/900,605

(22) PCT Filed: Jun. 19, 2014

(86) PCT No.: PCT/IB2014/001557
§ 371 (c)(1),
(2) Date: Dec. 21, 2015

(87) PCT Pub. No.: WO2014/203076
PCT Pub. Date: Dec. 24, 2014

(65) Prior Publication Data
US 2016/0136315 A1    May 19, 2016

(30) Foreign Application Priority Data
Jun. 19, 2013    (BR) .......................... 1320130154163

(51) Int. Cl.
| | | |
|---|---|---|
| *A61L 9/22* | (2006.01) | |
| *A61L 2/14* | (2006.01) | |
| *A61L 9/20* | (2006.01) | |
| *B60H 3/00* | (2006.01) | |
| *A61L 2/08* | (2006.01) | |
| *F24F 3/16* | (2006.01) | |
| *B01D 53/00* | (2006.01) | |
| *B01D 53/32* | (2006.01) | |

(52) U.S. Cl.
CPC ................. *A61L 2/14* (2013.01); *A61L 2/088* (2013.01); *A61L 9/20* (2013.01); *A61L 9/205* (2013.01); *A61L 9/22* (2013.01); *B60H 3/0078* (2013.01); *B60H 3/0085* (2013.01); *B60H 3/0092* (2013.01); *B01D 53/007* (2013.01); *B01D 53/32* (2013.01); *B01D 2259/4566* (2013.01); *B01D 2259/4575* (2013.01); *B01D 2259/804* (2013.01); *B01D 2259/818* (2013.01); *F24F 2003/1667* (2013.01)

(58) Field of Classification Search
CPC ............... A61L 9/20; A61L 9/205; A61L 9/22
USPC ....................................................... 422/122
See application file for complete search history.

(56) References Cited

U.S. PATENT DOCUMENTS

| | | | | |
|---|---|---|---|---|
| 6,773,682 B1 * | 8/2004 | Benda | ........................ | A61L 9/00 422/186.3 |
| 2005/0063881 A1 * | 3/2005 | Senne | ................... | B01D 53/007 422/186.3 |

* cited by examiner

*Primary Examiner* — Sean E Conley
(74) *Attorney, Agent, or Firm* — Howison & Arnott, LLP

(57) ABSTRACT

An object of this certificate of addition includes the compaction of the equipment into two modules (1 and 2) on a smaller scale so as to enable the installation of the modules directly in the air conditioning system of transportation vehicles or other means of transportation.

2 Claims, 3 Drawing Sheets

EQUIPMENT FOR SANITIZING THE AIR CONDITIONING SYSTEM OF VEHICLES BY MEANS OF RADIANT CATALYTIC IONIZATION

CROSS-REFERENCE TO RELATED APPLICATIONS

This application is a U.S. National Phase application submitted under 35 U.S.C. §371 of Patent Cooperation Treaty application serial no. PCT/IB14/01557 filed Jun. 19, 2014, entitled EQUIPMENT FOR SANITIZING THE AIR CONDITIONING SYSTEM OF VEHICLES BY MEANS OF RADIANT CATALYTIC IONIZATION, which application claims priority to Brazilian Patent Application No. 1320130154163, filed Jun. 19, 2013, which is a Certificate of Addition of and claims priority from and/or benefit of Brazil Patent Application No. 1020120011220, filed 17 Jan. 2012. This application also incorporates by reference Brazil Patent Application No. 1020120011220.

Patent Cooperation Treaty application serial no. PCT/IB14/01557, published as WO/2014/203076, and Brazilian Patent Application No. 1320130154163 are incorporated herein by reference.

TECHNICAL FIELD

This application relates to equipment for sanitizing the air conditioning system and interior of vehicles in general through the transformation of the ambient air into a purifying plasma primarily containing hydrogen peroxide and hydroxyl radicals.

SUMMARY

In BR 102012001122-0—the generation of the plasma is achieved through the phenomenon of radiant catalytic ionization, when air passes through a UVX lamp enclosed by a hive impregnated with noble metals, with emphasis on titanium dioxide.

In BR 102012001122-0—the air is drawn into the interior of the equipment by means of a fan adjacent to a protective grating which is activated simultaneously with the UVX lamp when the ON-OFF switch is switched on.

In BR 102012001122-0—the application of the plasma for a predetermined period of time can be performed at two different speeds selected with a control button.

In BR 102012001122-0—the portability of the equipment facilitates the maneuverability and positioning thereof directly on the interior of the vehicle where it takes place or in the inlet region for air conducted to the air conditioning system.

Using the same inventive concept as BR 102012001122-0, this certificate of addition provides for the compacting of the equipment in two modules with the purpose of being used onboard automobiles and other means of transportation. By virtue of a more compact design, it is possible to perform the installation of the UVX lamp module by incorporating and/or installing it at a strategic point along the path traveled by the air used in the air-conditioning of the vehicle.

The tables below show tests that corroborate the efficacy of the equipment when employed in a passenger vehicle in terms of the concentration of fungi and bacteria, and the measurement of direct readings for temperature, humidity, volatile organic compounds, carbon monoxide, particulate matter and formaldehydes. The tests were conducted on two vehicles—one with the equipment and one without it.

TABLE 1

Fungi tests
Environmental monitoring and control of possible colonization, multiplication and dissemination of fungi in the interior ambient air.

| Characterization of sampling (sampling plan) | Sample no. Recommended rates | Ambient air ($CFU/m^3$) ≤750 | Outside air ($CFU/m^3$) 0 | I/E ratio Ambient air/air (limit ≤1.5) | Genera of fungi isolated |
|---|---|---|---|---|---|
| Golf PXX1444- with treatment | 31484/12 | 17 | 1734 | 0.0 | *Cladosporium* sp.; *Penicillium* sp.; *Rhodotorula* sp.; *Phoma* sp.; *Alternaria* sp. |
| Fiesta DAI4309- without treatment | 31485/12 | 34 | 1734 | 0.0 | *Cladosporium* sp.; *Penicillium* sp.; *Rhodotorula* sp. |

Note 1:
The tests above were performed in accordance with the requirements of Resolution-RE no. 09 of MS/ANVISA of 16 Jan. 2003.

TABLE 2

Test for bacteria
Environmental monitoring and control of possible colonization, multiplication and dissemination of bacteria in the interior ambient air.

| Characterization of sampling (sampling plan) | Sample no. Recommended rates | Ambient air ($CFU/m^3$) ≤750 | Outside air ($CFU/m^3$) 0 | I/E ratio Ambient air/air (limit ≤1.5) |
|---|---|---|---|---|
| Golf PXX1444- with treatment | 31482/12 | 315 | 331 | 1.0 |

TABLE 2-continued

Test for bacteria
Environmental monitoring and control of possible colonization,
multiplication and dissemination of bacteria in the interior ambient air.

| Characterization of sampling (sampling plan) | Sample no. Recommended rates | Ambient air (CFU/m$^3$) ≤750 | Outside air (CFU/m$^3$) 0 | I/E ratio Ambient air/air (limit ≤1.5) |
|---|---|---|---|---|
| Fiesta DAI4309- without treatment | 31483/12 | 772 | 331 | 2.3 |

TABLE 3

Evaluation of temperature, humidity, volatile organic compounds, carbon monoxide, particulate matter and formaldehydes.

| Site | Temperature ° C. | Humidity (%) | VOCs g/m$^3$ | Carbon monoxide (ppm) | Aerosols µg/m$^3$ | Formaldehydes ppm |
|---|---|---|---|---|---|---|
| Recommended rates | 0 | 0 | 500.0 | See note 3 | 50 | 2[cropped] |
| Outside air | 29.5 | 41.9 | 835.7 | 3.9 | 77.3 | < [cropped] |
| Golf PXX1444 - with treatment | 22.6 | 52.4 | 432.8 | 0.5 | 6.3 | < [cropped] |
| Fiesta DAI4309 - without treatment | 24.1 | 52.1 | 624.7 | 1.3 | 62.5 | 50[cropped] |

Note 2:
The tests above were performed in accordance with the requirements of the Green Building Council, IEQ Credit 3.2
Note 3:
According to Green Building Council, IEQ Credit 3.2, the recommended rate must be 9 ppm and not more than 2 ppm greater than the outside concentration.

BRIEF DESCRIPTION OF THE DRAWINGS

Below, the certificate of addition will be explained with reference to the enclosed drawings, which are presented for illustrational purposes and are not limitative.

DETAILED DESCRIPTION

Figure 1:
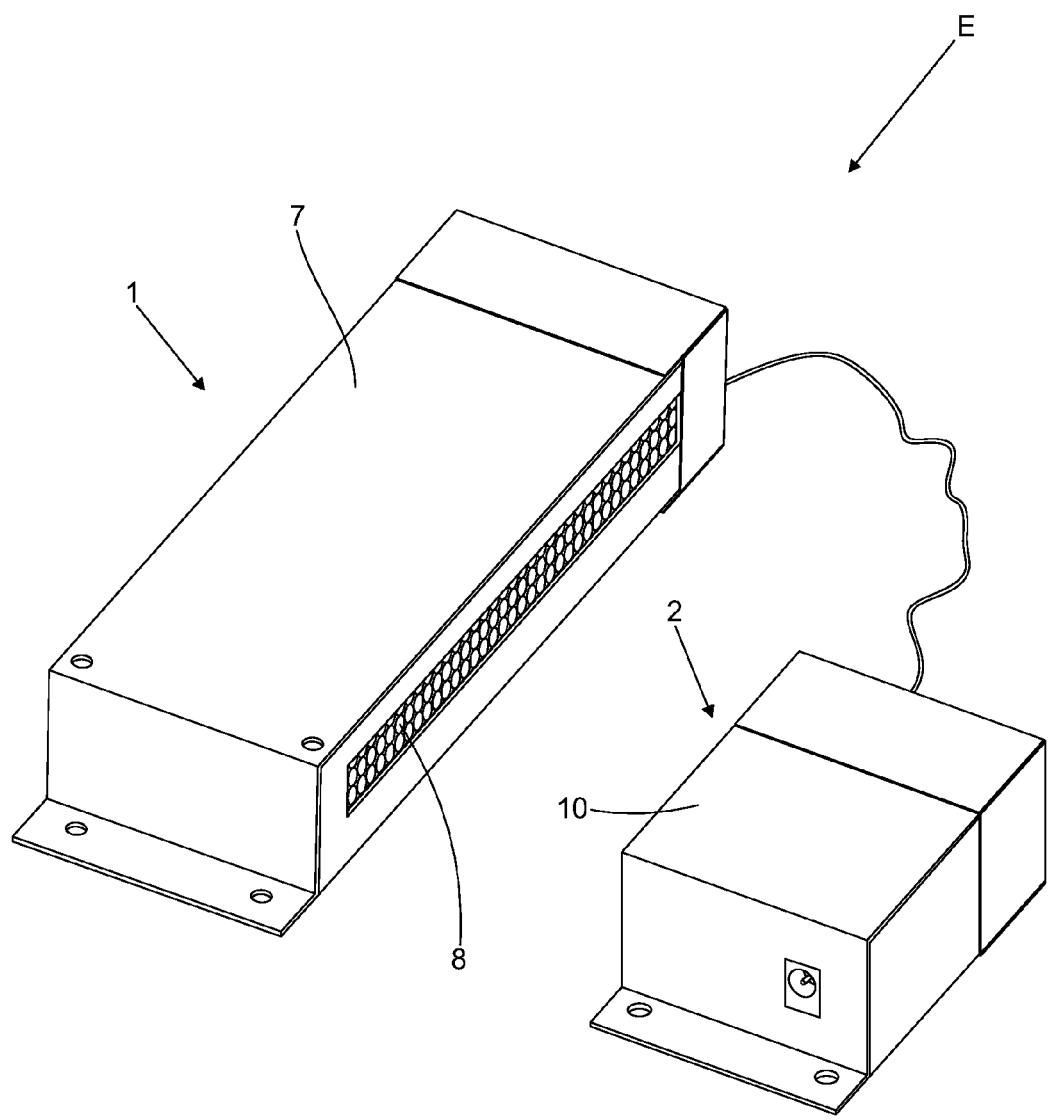
FIG. 1: Schematic perspective view of the equipment.
Figure 2:
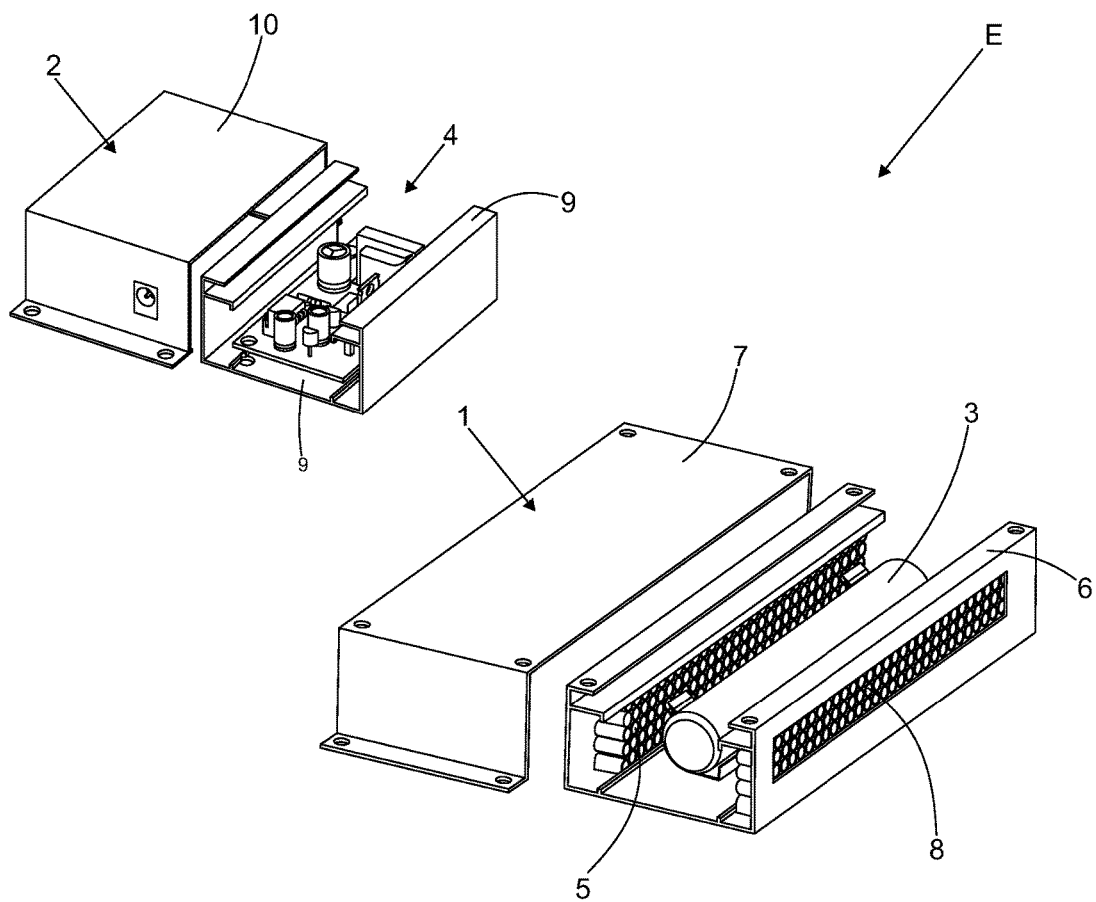
FIG. 2: Exploded schematic perspective view of the equipment.
Figure 3:
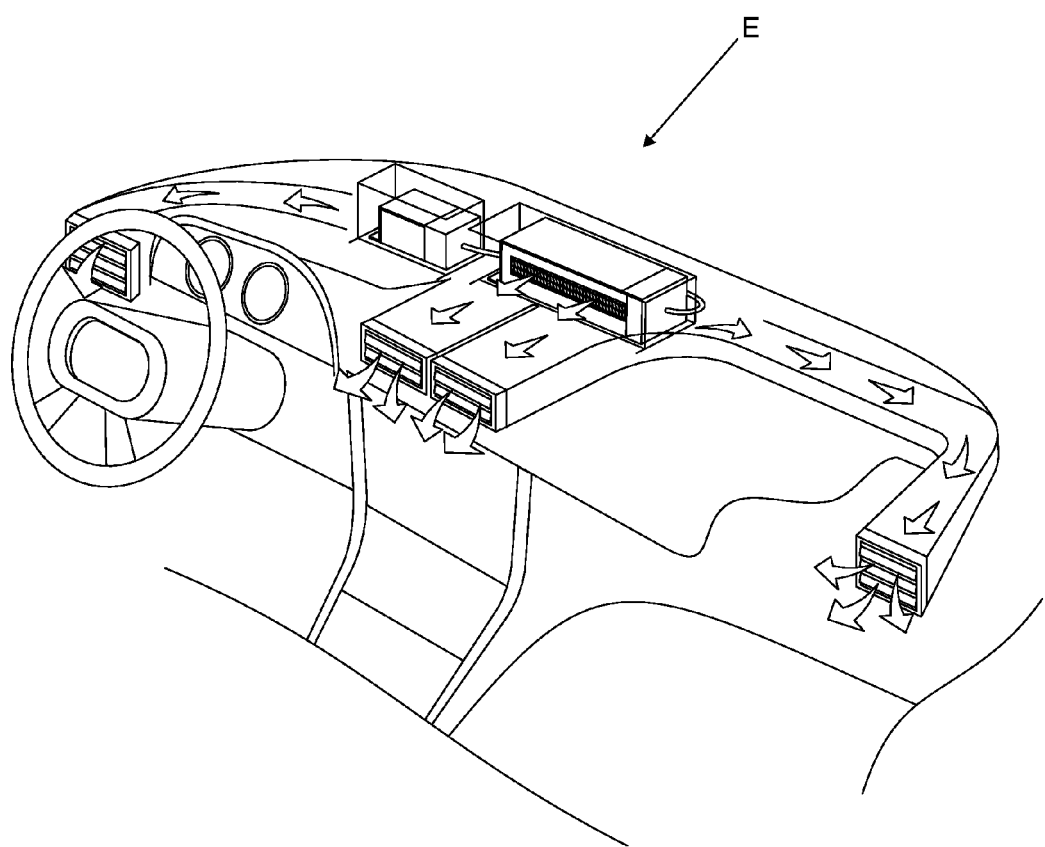
FIG. 3: Schematic perspective view of the equipment showing a use condition.

The "EQUIPMENT FOR SANITIZING THE AIR CONDITIONING SYSTEM OF VEHICLES BY MEANS OF RADIANT CATALYTIC IONIZATION" which is an object of this certificate of addition includes the compacting of the equipment into two modules (1 and 2) on a scale small enough so as to enable installation of the modules directly in the air conditioning system of transportation vehicles or other means of transportation.

More particularly, the equipment (E) of this addition of compact design is best represented by a module (1) containing the UVX lamp (3), and another module (2) with the cell (4) with the respective components responsible for the powering and controlling the functions of the lamp itself. Such modules (1 and 2) are preferably distinct so as to enable installation of module (1) of the UVX lamp (3) at a strategic point [along the path] traveled by the air used in the air-conditioning of the vehicle. Thus, when the air passes through the UVX lamp (3) and the hive (5), which is impregnated or coated with a noble metal alloy. The air coming from the forced ventilation of the vehicle undergoes a radiant catalytic ionization reaction, generating purifying plasma with a high level of sanitizing power, not just for the air conditioning system, but for sanitizing the entire vehicle compartment. The first module (1) comprises of a frame (6) with covering (7) and lateral outlets (8) for the passage of air through the hives (5) and the UVX lamp (3), whereas the second module (2) is also formed by frame (9) and covering (10) receiving the components of the cell (4).

In this context, when the air conditioning system is switched on, the UVX lamp (3) is lit, thus bringing about the transformation of the air into purifying plasma composed of hydroxyl radicals and hydrogen peroxide. The purifying plasma can be applied according to the ventilation speeds of the air conditioning system of automobiles, and its respective resources, depending on the vehicle.

Moreover, the equipment (E) can also be applied in the air conditioning systems of other land, sea or air vehicles such as, for example, trains, subways, boats, airplanes, etc.

What is claimed is:

1. A device comprising:
  a first module comprising:
    a UVX lamp configured to produce UV light;
    a first and a second hive structure each impregnated with a noble metal alloy and configured to generate, via a radiant catalytic ionization reaction with the UV light, a purifying plasma comprising oxidative sanitizing molecules; the first hive structure being positioned along a first longitudinal side of the UVX lamp, and the second hive structure being positioned along a second longitudinal side of the UVX lamp;
    a first frame on which the UVX lamp and the first and the second hive structures are mounted; and
    a first cover portion that combines with the first frame to establish an exterior covering about the first module and provide cut-away portions that enable lateral passage of air in and out of the first module through the first and the second hive structures when the first module is positioned within an air duct of an air conditioning system of a transportation vehicle; and
  a second module located remotely from the first module, the second module being connected to the first module by an electrical connection, the second module comprising:

a cell that includes components that power and control the functions of the UVX lamp;

a second frame to which the cell is mounted; and a second cover portion that combines with the second frame to establish an exterior covering about the second module;

wherein the second module is configured to be positioned within or proximate to a control console of the transportation vehicle while being remote from the first module.

2. The device of claim 1, wherein the transportation vehicle is an automobile and the control console is a dashboard of the automobile.

\* \* \* \* \*